United States Patent [19]

Garman

[11] Patent Number: 4,935,465
[45] Date of Patent: Jun. 19, 1990

[54] CONJUGATES OF PHARMACEUTICALLY USEFUL PROTEINS

[75] Inventor: Andrew J. Garman, Betchworth, United Kingdom

[73] Assignee: Beecham Group p.l.c., England

[21] Appl. No.: 802,663

[22] Filed: Nov. 27, 1985

[30] Foreign Application Priority Data

Nov. 30, 1984 [GB] United Kingdom ................ 8430252

[51] Int. Cl.$^5$ ..................... C07K 17/06; C07K 17/08; A61K 37/54; A61K 37/465
[52] U.S. Cl. .................................. 525/54.1; 530/334; 530/402; 530/403; 530/404; 435/177; 435/180; 435/181
[58] Field of Search ............... 525/54.1; 530/334, 335, 530/336, 337, 402, 403, 404, 405, 406, 407, 408, 409, 410, 411; 435/174, 177, 180, 181

[56] References Cited

U.S. PATENT DOCUMENTS

| | | | |
|---|---|---|---|
| 4,055,635 | 10/1977 | Green et al. | 435/180 |
| 4,179,337 | 12/1979 | Davis et al. | 530/409 |
| 4,496,689 | 1/1985 | Mitra | 525/54.1 |
| 4,542,225 | 9/1985 | Blattler et al. | 548/473 |
| 4,569,789 | 2/1986 | Blattler et al. | 530/387 |
| 4,618,492 | 10/1986 | Blattler et al. | 424/85 |
| 4,640,835 | 3/1987 | Shimizu et al. | 424/94 |
| 4,764,368 | 8/1988 | Blattler et al. | 424/85 |
| 4,859,736 | 8/1989 | Rink | 525/54.1 |
| 4,863,735 | 9/1989 | Kohn et al. | 525/54.1 |

FOREIGN PATENT DOCUMENTS

| | | |
|---|---|---|
| 0038154 | 10/1981 | European Pat. Off. |
| 98110 | 1/1984 | European Pat. Off. |
| 2515684 | 5/1983 | France |
| 1059670 | 2/1967 | United Kingdom |
| 1390716 | 4/1975 | United Kingdom |

OTHER PUBLICATIONS

Means et al., Chemical Modification of Proteins, Holden-Day, San Francisco, 1971 pp. 76-77.
Patent Abstracts of Japan, vol. 8, No. 156 (C-234) [1593], 19th Jul. 1984.
G. Durand et al.: "Les Enzymes-Production et utilisations industrielles", part 1, 1982, pp. 81-118, Gauthier-Villars, Paris.
Chemical Abstracts, vol. 88, No. 22, 29th May 1978, p. 41, Abstract No. 153575h.
Shimizu et al., IXth International Congress On Thrombosis And Haemostasis, Stockholm, Jul. 3-8, 1983.

*Primary Examiner*—Nathan M. Nutter
*Attorney, Agent, or Firm*—Jacobs & Jacobs

[57] ABSTRACT

A conjugate comprising a pharmaceutically useful protein linked to at least one water-soluble polymer by means of a reversible linking group.

8 Claims, 5 Drawing Sheets

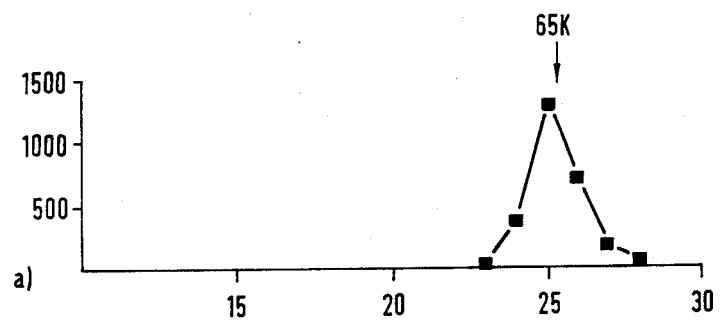
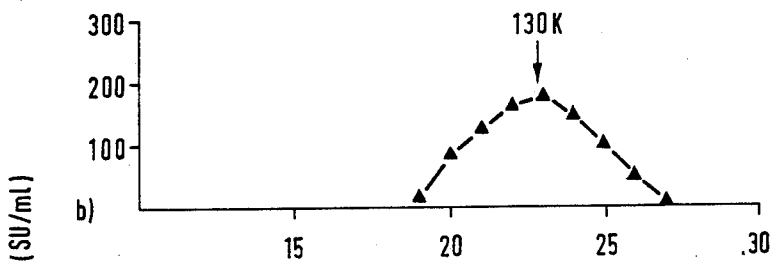
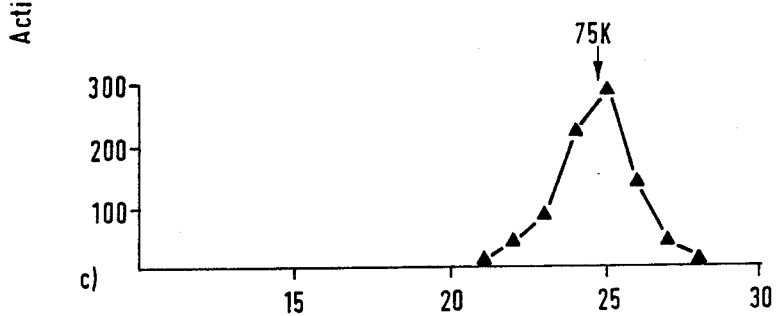
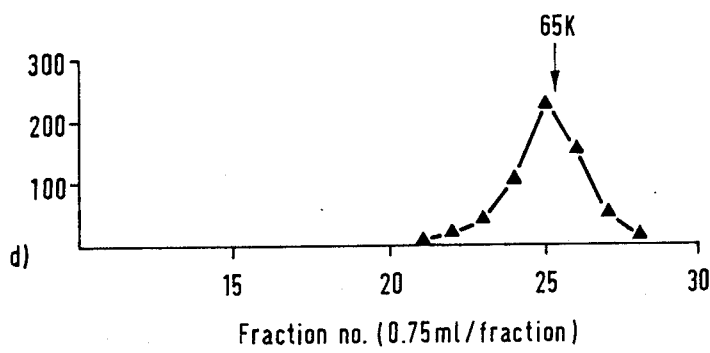
Fig.3a
Fig.3b
Fig.3c
Fig.3d

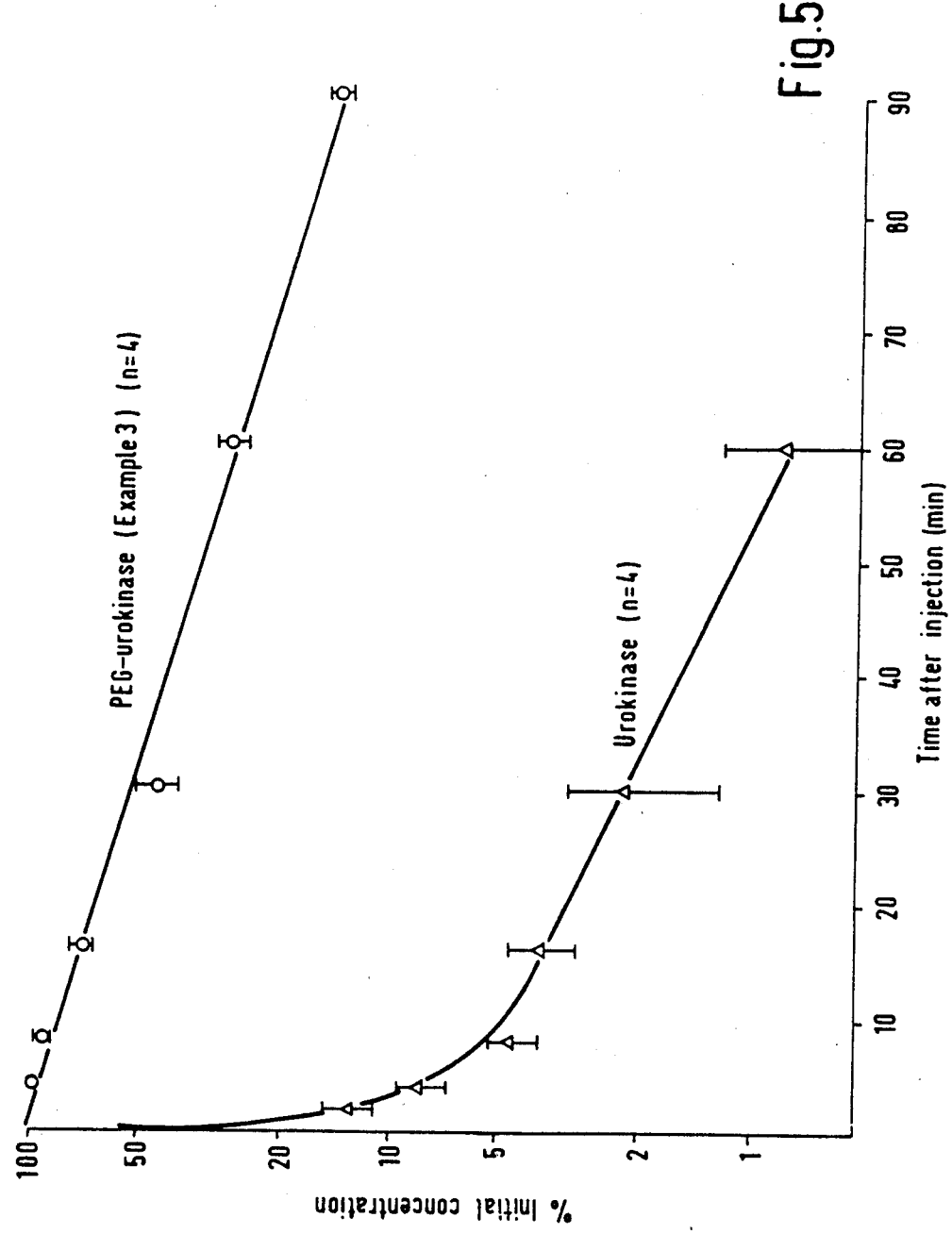

CONJUGATES OF PHARMACEUTICALLY USEFUL PROTEINS

This invention relates to conjugates of pharmaceutically useful proteins.

Conjugates of proteins and water soluble polymers have been prepared for a wide range of pharmaceutical purposes. Attachment of one or more polymer molecules usually has the effect of interfering with interactions between the protein and other macromolecules or cells. Thus the antigenicity or allergenicity of the protein is diminished or its clearance from the bloodstream is prolonged. For example, the plasma clearance of urokinase has been prolonged by the irreversible attachment of methoxy-polyethylene glycol. Alternatively, the conjugate may have novel properties: for example, European Patent No. 0,038,154 discloses conjugates of allergens with polysarcosine which have immunosuppressive properties.

The attachment of polymers to proteins to retard clearance or decrease antigenicity is of most use for proteins, usually enzymes, which act on low molecular weight substrates. If the protein, in order to produce a therapeutic effect, requires to act on a macromolecular or cell-bound substrate then it might be expected that the attachment of polymers would interfere with this interaction, resulting in a loss of activity. Such an effect has been demonstrated with streptokinase and polyethylene glycol where decreased antigenicity was only attained at the expense of a decrease in fibrinolytic activity. Frequently, even if the protein acts on low molecular weight substrates, a decrease in activity upon polymer attachment is encountered.

According to the present invention there is provided a conjugate comprising a pharmaceutically useful protein linked to at least one water-soluble polymer by means of a reversible linking group.

As used herein, the expression "pharmaceutically useful protein" means a protein which produces a therapeutic or pharmacological effect in the human or animal body.

The expression "reversible linking group" means a linkage which is broken under in vivo conditions at a clinically useful rate. Suitably the pseudo-first order rate constant for breakage of the linking group will be in the range of from $10^{-6}$ to $10^{-3}$ sec$^{-1}$.

This type of conjugate gives rise to sustained release of active protein.

BRIEF DESCRIPTION OF THE DRAWINGS

The present invention is illustrated by the accompanying drawings, in which:

FIGS. 3a–3d are hplc gell filtration elution profiles of tPA and the tPA conjugate of Example 4;

FIG. 5 shows the clearance of fibrinolytic activity of UK and of the UK conjugate of Example 3.

Figure 1:
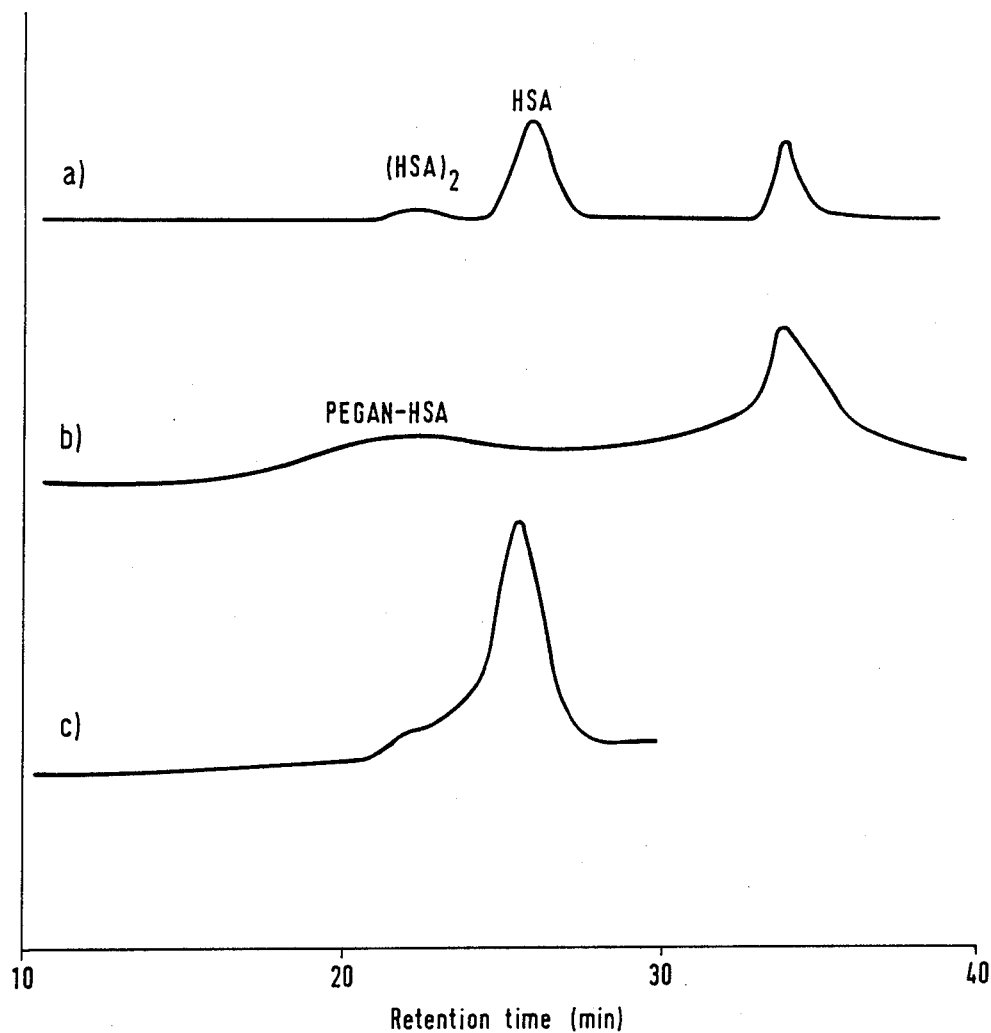
FIG. 1 shows elution profiles of human serum albumin (HSA) and of the HSA conjugate according to Example 2.

The conjugates may be represented by the general formula (I):

$$P-L-X \qquad (I)$$

wherein
P is a water-soluble polymer;
L is a reversible linking group; and
X is a pharmaceutically useful protein.

The number of water-soluble polymer molecules which can be linked to the protein in this way and which will remove the undesirable property (for example, antigenicity, fast clearance) depends upon the nature of the protein and can be determined by routine methods. However, the degree of modification of the protein by the reversible linkage of the polymer molecules (i.e. the number of polymer molecules linked to the protein) is of less importance than in the case of irreversible polymer protein conjugates.

Each protein molecule may have more than one linking group attached to it, and each linking group may have more than one water-soluble polymer attached thereto.

The molecular weights of the water-soluble polymers (P) should preferably be in the range 500 to $10^6$, most preferably in the range 2,000 to 20,000.

Examples of a suitable water-soluble polymer (P), include the polyamino-acids or polyimino-acids such as polysarcosine, poly-D,L-alanine, polyhydroxyproline, or the polysaccharides and their derivatives, for example, dextran, hydroxyethyl-starch or Ficoll, or optionally derivatised synthetic polymers such as polyethylene glycol, polypropylene glycol, the polyvinyl-pyrrolidones, the polyvinylalcohols or the polyacrylamides.

Suitably the water-soluble polymer (P) is methoxy polyethylene glycol.

The pharmaceutically useful protein (X) may be an enzyme, a pro-enzyme or a non-enzymatic protein.

Suitable non-enzymic proteins include the interferons, the lymphokines particularly interleukin-2 , Protein A from *Staphylococcus aureus,* or hormones such as insulin, growth hormone or proteins which are used in vaccines such as allergen extracts, or viral coat proteins.

Examples where the pharmaceutically useful protein (X) is an enzyme or pro-enzyme include the proteases (together with their pro-enzymes) which are involved in haemostasis, fibrinolytic enzymes and their pro-enzymes, arginase, uricase, asparaginase, glutaminase, superoxide dismutase and enzymes which are absent in patients suffering various enzyme deficiency diseases, for example hexosaminidase A and glucocerebrosidase.

In a particularly preferred embodiment the pharmaceutically useful protein (X) is a fibrinolytic enzyme or pro-enzyme thereof.

The term "fibrinolytic enzyme" as used herein means any enzyme which demonstrates in-vivo fibrinolytic activity as defined in European Patent No. 0,009,879 (U.S. Pat. No. 4,285,932).

These enzymes may be prepared by tissue culture, extraction from blood, urine or tissues, or by recombinant DNA methodologies.

Examples of such enzymes are the plasminogen activators including tissue plasminogen activator such as melanoma plasminogen activator, urokinase (both high and low molecular weight and the single chain form), and complexes of streptokinase with plasmin Suitable pro-enzymes include pro-urokinase and pro-tissue plasminogen activator.

The class of pharmaceutically useful proteins defined above as fibrinolytic enzymes and pro-enzymes thereof also includes:

(a) the fibrinolytically active hybrid proteins as disclosed in European Published Application No. 0155387;

(b) the derivatives of fibrinolytic enzymes as disclosed in European Published Application No. 0155388; and (c) the protein conjugates as disclosed in European Published Application No. 0152736.

The fibrinolytic enzymes may optionally be blocked at their active centers as described in the European Patent No. 0,009,879 (U.S. Pat. No. 4,285,932).

The linking group (L) is such that the linkage is broken under in vivo conditions at a clinically useful rate.

The cleavage of the linking group (L) may occur by hydrolysis or by intra-molecular rearrangement. It may take place within the linking group (L) itself or at the boundary of the linking group (L) with the polymer or with the protein.

Preferably the cleavage should give rise to unmodified protein.

A suitable linking group (L) is based on substituted maleic acids. The conjugates formed can be represented by the general formula (II):

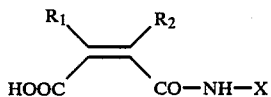
(II)

where X is as hereinbefore defined and the NH moiety is derived from a protein amino group in X; and either:

(i) $R_1$ and $R_2$ are each a non-polymeric organic group or a group of formula —$R_3$—P wherein P is as hereinbefore defined and $R_3$ is a bridging group; or (ii) $R_1$ and $R_2$ together are $C_{3-5}$ polymethylene to complete a 5- to 7-membered alicyclic ring or together complete an aromatic ring, wherein the alicyclic or aromatic ring is substituted by groups $R_4$ and $R_5$ which are each a non-polymeric organic group or a group of formula —$R_3$—P;
provided that at least one of $R_1$ and $R_2$ or of $R_4$ and $R_5$ is a group —$R_3$—P.

In neutral and acidic solutions, including physiological condition of pH 7.4 and 37° C., the CO—NH bonds in the conjugate of formula (II) are hydrolysed by a process that is facilitated by the adjacent carboxyl function, thereby giving rise to an unmodified protein. The rate of deacylation depends on the atoms near to the double bond, the nature of which is not important provided that the deacylation rate is not altered detrimentally.

Examples of suitable bridging groups $R_3$ include straight or branched $C_{1-10}$ aliphatic hydrocarbon-chains which are optionally interrupted or terminated by an amide or ester moiety or by at least one hetero atom selected from oxygen, sulphur or nitrogen, optionally substituted by a $C_{1-6}$ alkyl group.

Preferably $R_3$ contains an electron donating moiety adjacent to the double bond, such as methylene.

Examples of suitable groups —$R_3$—P include P—$(CH_2)_n$—, PO$(CH_2)_n$, PO—, P$(CH_2)_nO$—, CH$(CH_3)$P—, C$(CH_3)_2$P, —CH$(CH_3)$OP or —C$(CH_3)_2$OP, where n is an integer of from 1 to 6.

Suitable non-polymeric organic groups for $R_1$, $R_2$, $R_4$ and $R_5$ include aliphatic $C_{1-10}$ hydrocarbon groups optionally interrupted or terminated by a heteroatom selected from oxygen, sulphur or nitrogen optionally substituted by a $C_{1-6}$ alkyl group.

Preferably the non-polymeric organic group contains an electron donating moiety adjacent to the double bond, such as methylene or methyl.

Examples of such groups for $R_1$, $R_2$, $R_4$ and $R_5$ include $R_6$, $R_6$—O— or $(R_6)_2$N—, wherein $R_6$ is straight or branched $C_{1-6}$ alkyl.

In particular $R_1$, $R_2$, $R_4$ or $R_5$ could be $CH_3$, $CH_3CH_2$—, $(CH_3)_2CH$—, $CH_3CH_2CH_2$—, $(CH_3)_3C$—, $CH_3O$—, $CH_3CH_2O$— or $(CH_3)_2N$—.

There is a sub group of conjugates within formula (II) of formula (IIA), in which $R_1$ and $R_2$ are each a non polymeric organic group or a group of formula —$R_3$—P as hereinbefore defined provided that at least one of $R_1$ and $R_2$ is a group —$R_3$—P.

In conjugates of formula (IIA), preferably one of $R_1$ and $R_2$ is a group P—$CH_2$— and the other is methyl.

Examples of conjugates of formula (II) wherein $R_1$ and $R_2$ are joined together included cyclic structures of formula (IIB):

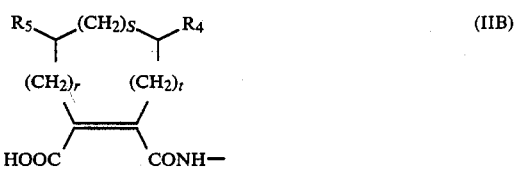
(IIB)

wherein r, s and t are each independently zero, one or two provided that r+s+t is greater than 0 and less than 4, i.e. an integer of 1 to 3, and $R_4$ and $R_5$ are as hereinbefore defined Alternatively $R_1$ and $R_2$ may be joined together to form an aromatic structure Examples of such conjugates of formula (II) include conjugates of formula (IIC):

(IIC)

wherein $R_4$ and $R_5$ are as defined above in relation to formula (II).

Suitable non-polymeric organic groups for $R_4$ or $R_5$ in formulae (IIB) and (IIC) include those described above under formula (II).

Further according to the present invention there is provided a process for preparing a conjugate as described above, which process comprises reacting a pharmaceutically useful protein with a water-soluble polymer-containing reagent comprising a group which is capable of reacting with a protein amino group or derivative thereof, to form a reversible linking group as hereinbefore defined.

The polymer-containing reagent may be represented by the formula (III):

P—L¹     (III)

wherein P is as hereinbefore defined and $L^1$ is a group which is capable of forming a linking group (L) as aforesaid.

The conditions used to prepare the conjugates will depend on the nature of the polymeric reagent, the protein and the stability of the linkage formed and will be apparent to the skilled man.

Suitably, the protein is dissolved in an aqueous buffer preferably at a moderately alkaline pH e.g. pH 7.0–9.5 and at a temperature in the range 0°–40° C. The pH may be controlled, if necessary, by acid or base addition, either manually or automatically, during the reaction.

The amount of the water-soluble polymer-containing reagent (formula (III)) used determines the number of polymer molecules which become attached to the protein. At least a molar excess of reagent (formula (III)) should be added.

After the reaction is complete, excess reagent and unwanted reaction products may be removed. Suitable removal techniques include ammonium sulphate precipitation, dialysis, diafiltration or a number of chromatographic procedures, for example, gel filtration, ion-exchange chromatogrally, hydrophobic interaction chromatography or affinity chromatography.

For fibrinolytic enzymes and other serine proteases, affinity chromatography on benzamidine. Sepharose is a particularly preferred procedure.

For fibrinolytic enzymes optional blocking at their active centers may be performed either before or after the polymer conjugation reaction.

The type of linkage illustrated in the conjugate of formula (II) is suitably obtained by reaction of reagents of formula (IV):

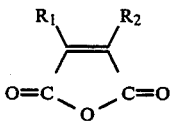

(IV)

wherein $R_1$ and $R_2$ are as hereinbefore defined, with an amino group of a pharmaceutically useful protein.

It will be appreciated that the conjugate of formula (II) thus formed will exhibit isomerism at the linkage if $R_1 = R_2$ since the protein amino group could, in principle, react with either carbonyl group.

Reagents of formulae (III) and (IV) are novel and as such form part of the invention.

A reagent of the formula (IV) may be prepared by the reaction of a compound of formula (IVA):

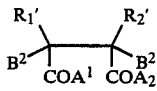

(IVA)

where $A^1$ and $A^2$ are each hydroxy groups or together are —O—, $B^1$ and $B^2$ together are a bond or are groups susceptible to elimination to form a bond, and either:

(i) $R_1'$ and $R_2'$ are each a non-polymeric organic group as hereinbefore defined or a group W; or (ii) $R_1'$ and $R_2'$ together are $C_{3-5}$ polymethylene to complete a 5- to 7-membered alicyclic ring or together complete an aromatic ring, wherein the alicyclic or aromatic ring is substituted by groups $R_4'$ and $R_5'$ which are each a non-polymeric organic group as hereinbefore defined or a group W provided that at least one of $R_1'$ and $R_2'$ or of $R_4'$ and $R_5'$ is a group W;

with a compound PY (formula IVB) where P is as hereinbefore defined; wherein groups W and Y are capable of reacting together to provide a bridging group $R_3$;

and thereafter when $A^1$ and $A^2$ are each hydroxy, dehydrating the product of the reaction and/or when $B^1$ and $B^2$ are groups susceptible to elimination, subjecting the product of the reaction to elimination.

Preferably in the compound of formula (IVA), groups $A^1$ and $A^2$ together are —O— and groups $B^1$ and $B^2$ together are a bond.

The nature of the groups W and Y and consequently the reaction conditions employed, is determined by the bridging group $R_3$ to be provided.

Where the bridging group is an aliphatic hydrocarbon chain containing a heteroatom as aforesaid, the groups Y and W are each hydrocarbon chains of appropriate length and terminated respectively by the appropriate nucleophilic heteroatom O, S or N and a suitable leaving group such as halide (preferably bromo or iodo), methanesulphonyl or 4-toluenesulphonyl. Where the bridging group $R_3$ is a aliphatic hydrocarbon chain, the group Y is a terminal nucleophilic heteroatom on the polymer P and the group W is the corresponding hydrocarbon chain derivatised by a suitable leaving group. The reaction conditions for the nucleophilic displacement of the leaving group in these cases are conventional and will be determined mainly by the polymer. Thus, when the nucleophile is —O—, the reaction may be carried out in any refluxing non-polar solvent under an atmosphere of dry nitrogen until the reaction is complete.

Where the bridging group is a aliphatic hydrocarbon chain containing an amide or ester moiety, the groups W and Y are each hydrocarbon chains of appropriate length, one terminated by a carboxyl function and the other by an hydroxyl or an amino function. The reaction conditions are conventional conditions for the formation of a ester or amide linkage, such as by activating the acid under non-aqueous conditions with a suitable activator, for example dicyclohexylcarbodiimide, and subsequent reaction with the appropriate alcohol or amine.

The derivatisation of the polymer P to give a compound of formula (IVB) may be carried out by conventional procedures, as may the preparation of a compound of formula (IVA).

A particularly suitable reagent of formula (IV) is the anhydride of formula (V):

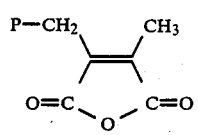

(V)

wherein P is as hereinbefore defined.

The mode of attachment of the water-soluble polymer (P) to the linking group (L) will depend on the chemical nature of the polymer. Thus if P is methoxypolyethylene glycol in formula (V), the reagent is suitably of formula (VI):

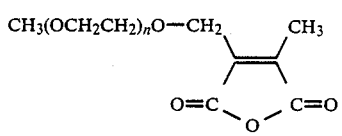

(VI)

If the polymer is polysarcosine, a suitable reagent is of formula (VII):

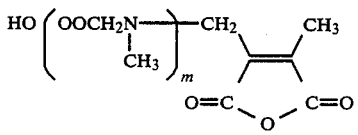

(VII)

In formulae (VI) and (VII), n and m are each integers such that the molecular weight of the polymer falls within the above described range.

Other polymers may have to be derivatised in conventional manner before a suitable connection to the linking group can be made.

A further suitable reagent of formular (IV) is the anhydride of formula (VIII):

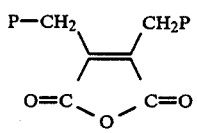

(VIII)

wherein P is as hereinbefore defined.

The mode of attachment of the P groups will be as described above under formula (IV).

The protein conjugate of this invention is preferably administered as a pharmaceutical composition.

Accordingly, the present invention also provides a pharmaceutical composition comprising the conjugate of the invention in combination with a pharmaceutically acceptable carrier.

The compositions will generally be formulated in the same or similar manner to the formulated proteins per se. This may include tablets, capsules, creams, syrups, suspensions, solutions, reconstitutable powders and sterile forms suitable for injection or infusion. Such compositions may contain pharmaceutically acceptable materials such as diluents, binders, colours, flavours, preservatives, disintegrates and the like in accordance with conventional pharmaceutical practices.

The protein in the composition of the invention will normally be administered at approximately the amount at which it is conventionally used. The mg/kg dosage is adjusted appropriately upwards to take account of the polymer molecules linked thereto, and the potency and pharmacokinetics of the conjugate.

When the pharmaceutically useful protein (X) is a fibrinolytic enzyme, the compositions according to the invention are formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubilising agent to keep the conjugate in solution and a local anaesthetic such a lignocaine to ease pain at the site of injection. Generally, the conjugate will be supplied in unit dosage form for example as a dry powder or water free concentrate in a hermetically sealed container such as an ampoule or sachette indicating the quantity of protein in activity units, as well as an indication of the time within which the free protein will be liberated. Where the conjugate is to be administered by infusion, it will be dispensed with an infusion bottle containing sterile pharmaceutical grade 'Water for Injection' or saline. Where the conjugate is to be administered by injection, it is dispensed with an ampoule of sterile water for injection. The injectable or infusable composition will be made up by mixing the ingredients prior to administration.

The precise dose to be employed and mode of administration must per force in view of the nature of the complaint be decided according to the circumstances by the physician supervising treatment. However, in general, a patient being treated for a thrombus with a fibrinolytic conjugate will generally receive a daily dose equivalent to a protein dose of from 0.001 to 3.00mg/kg$^{-1}$ of body weight either by injection in up to five doses or by infusion. A preferred dosage is from 50-100 mg per day.

No toxicity has so far been observed or is indicated within the above described dose ranges.

According to a further aspect of the invention there is provided a method of treating a sufferer in need of a pharmaceutically useful protein as hereinbefore defined, which method comprises administering to the sufferer an effective non-toxic amount of a protein conjugate of the invention.

In particular there is provided a method of treating thrombotic diseases, which comprises administering to the sufferer an effective non-toxic amount of a fibrinolytic enzyme conjugate as described above.

The invention also provides a conjugate of the invention for use as an active therapeutic substance. The invention further provides a conjugate in which the pharmaceutically useful protein is a fibrinolytic enzyme or pro-enzyme for use as an active therapeutic substance and in particular for use in the treatment of thrombotic diseases.

The following Examples illustrate the invention.

In the following Examples it is to be noted that there are two potential linkage points for the protein on the linking group (i.e. the two carboxyl functions of the maleic anhydride derivative), and no attempt has been made to distinguish between them although, for convenience, only one of the two potential isomers has been named and illustrated.

In the figures:

FIG. 1: G3000 SW HPLC elution profiles (OD$_{280}$)

(a) HSA (containing some dimer)

(b) The PEG-HSA reaction mixture (Example 2)

(c) The PEG-HSA peak after hydrolysis at pH 5.0, 37° C., 2 h.

Figure 2:
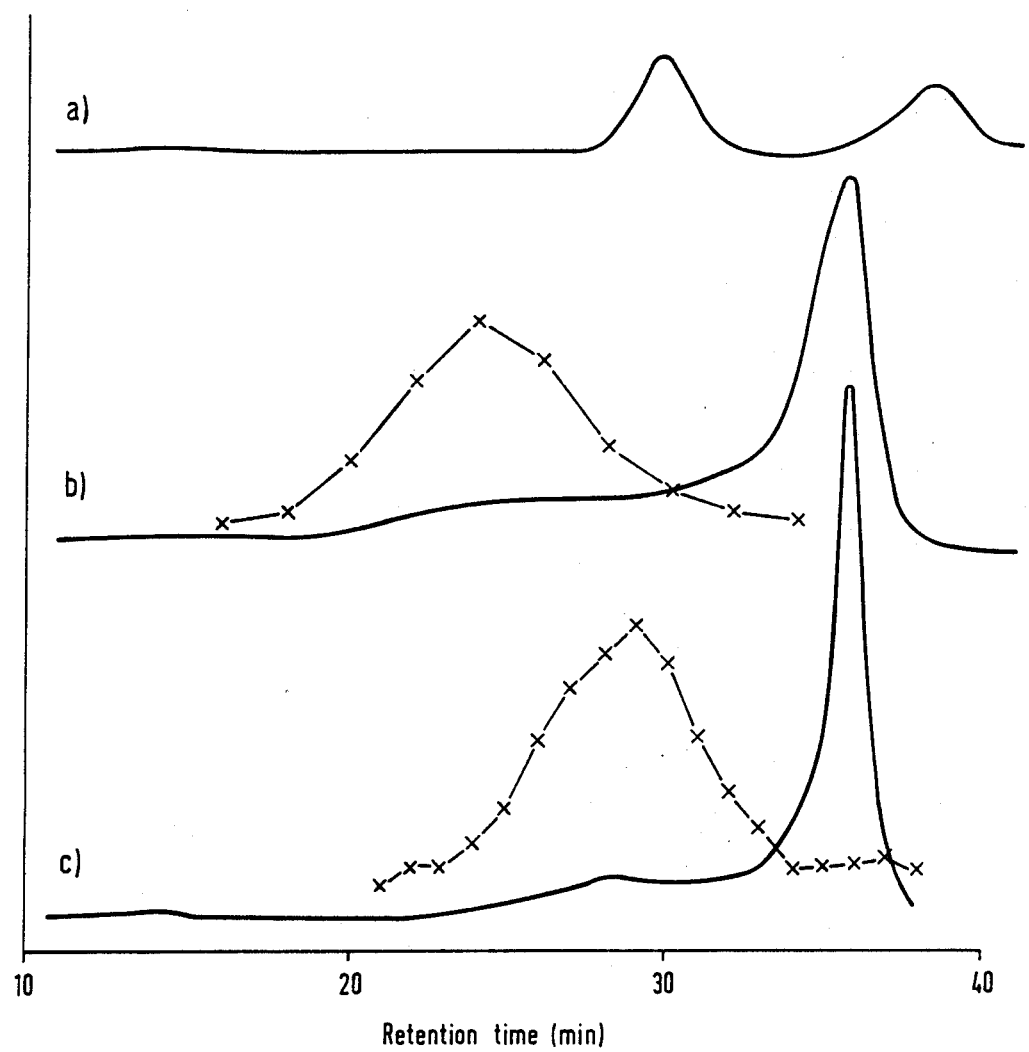
FIG. 2 shows elution profiles of urokinase (UK) and of the UK conjugate according to Example 2.

FIG. 2: G3000 SW HPLC elution profiles (OD$_{280}$,$^{125}$I)

(a) Urokinase (high molecular weight)

(b) The PEG-UK reaction mixture (Example 2)

(c) PEG-UK after hydrolysis at RT for 3 days —x—x— shows the $^{125}$I profile.

FIG. 3: Analytical hplc gel filtration elution profiles of:

(a) tPA, (b) the PEG-tPA conjugate (example 4), (c) the conjugate after 21 h at 37° C. and (d) the conjugate after 44 h at 37° C.

The apparent molecular weights shown are obtained from a calibration curve with Biorad standards.

Figure 4:
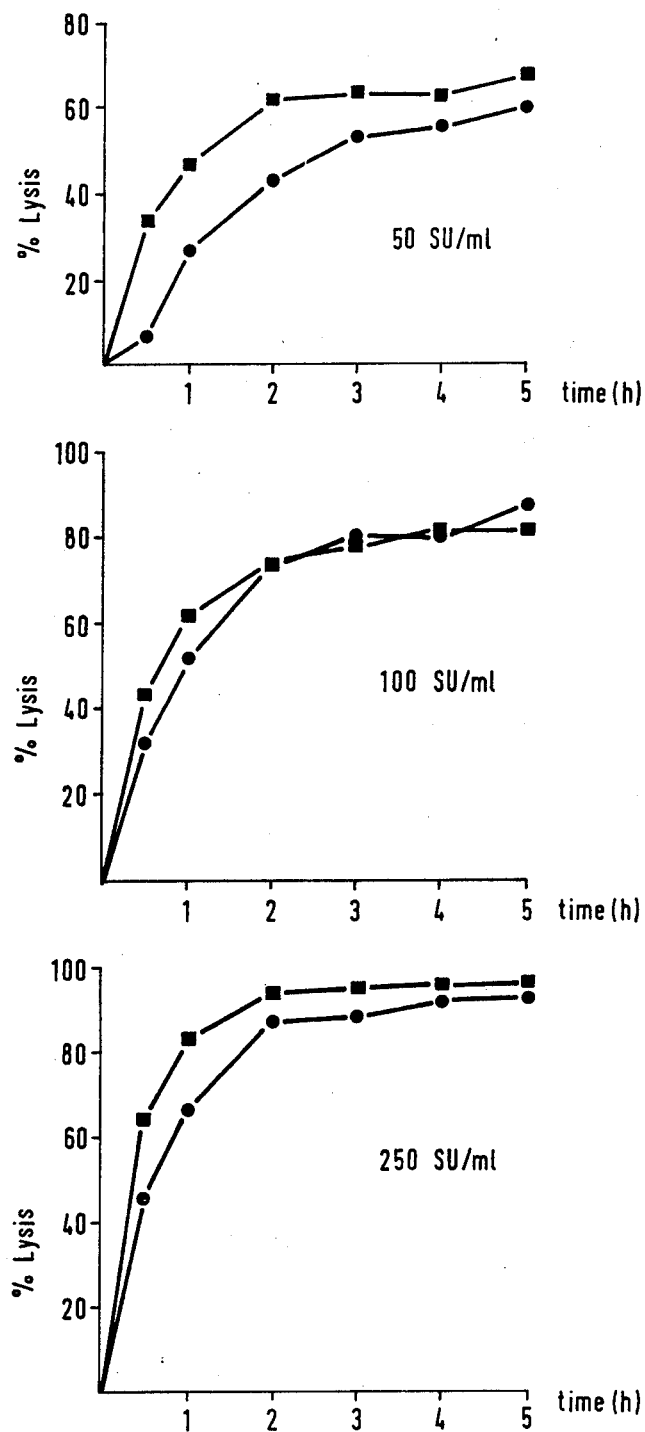
FIG. 4 shows the lysis of human clots using UK and the UK conjugate of Example 3.

FIG. 4: Time course of in vitro human clot lysis by urokinase (■) and PEG-urokinase (Example 3 ●)

FIG. 5: Clearance of fibrinolytic activity from guinea pig bloodstream.

EXAMPLE 1

Preparation of 2-(Methoxypolyethylene (5000) glycoxymethylene)-3-methyl maleic anhydride (i) To 2,3-dimethylmaleic anhydride (2.0 g, 15.9 mmole) in dry, redistilled carbon tetrachloride (30 ml) was added N-bromosuccinimide (5.72 g, 32 mmole) and benzoyl peroxide (5 mg). The stirred mixture was heated at a gentle reflux for 22 h. The solution was allowed to cool, and was filtered and evaporated to leave a brown oil (2.97 g). This was subjected to bulk to bulk distillation (170° C. at 1 mM Hg) to give a pale green oil (1.40 g). This was shown by 1H nmr to be ~85% of the desired monobromo derivative. Small traces of dibrominated and unbrominated material were also found to be present but as these could not readily be removed the material was used as isolated in further transformations.

$^1$H nmr (CDCl$_3$) δ 4.2 (CH$_2$ Br disubstituted material), 4.1 (CH$_2$ Br monosubstituted material), 2.2 (CH$_3$, monosubstituted material), 2.2 (CH$_3$ unsubstituted)

(ii) Dried Methoxy polyethylene glycol (5000) (11.7 g, 2.34 mmole) was added to a stirred mixture of sodium amide (91 mg, 2.34 mmole) in benzene (150 ml). The bromomethylanhydride (480 mg, 2.34 mmole) was added. The reaction was allowed to stir at reflux for 22 h. On cooling, the solution was filtered and petroleum ether (600 ml) was added. The solid that was precipitated was filtered and dried in vacuo to yield a wax (10 g). This was shown by difference infra red spectroscopy to contain the desired compound Little or no ring opening could be detected Further evidence of the structure was obtained by titration of a hydrolysed sample with NaOH: 1.08 moles anhydride/mole PEG was detected.

EXAMPLE 2

Preparation of 2-[ω-methoxypolyethyleneglycoxymethylene], 3-methylmaleyl-human serum albumin

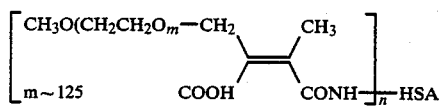

To a stirred solution of HSA (Sigma, 20 mg in 0.1 M sodium pyrophosphate/HCl, 0.01% Tween 80, pH 7.4 buffer (2.0 ml) at room temperature was added 2-(methoxypolyethylene (5000) glycoxymethylene)-3-methyl maleic anhydride (400 mg), maintaining the pH at 8.0 by addition of 0.1 M NaOH. After base uptake has ceased, a portion was analysed by HPLC gel filtration. The modified HSA eluted as a broad peak corresponding in appearent molecular weight to the albumin dimer viz. 130,000 (FIG. 1b). The relevant fractions were pooled.

Reversibility was studied at pH 5.0 since deacylation is more rapid at this pH. A portion of the conjugate pool was adjusted to pH 5.0 with dilute HCl and incubated at 37° C. After 2 h a portion was analysed by HPLC. FIG. 1c shows that essentially complete reversal had been achieved.

EXAMPLE 3

Preparation of 2-[ω-methoxypolyethyleneglycoxymethylene], 3-methylmaleyl-urokinase

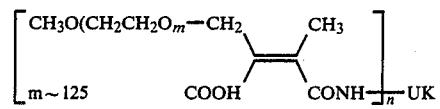

(i) To a stirred solution of urokinase (Serono, high MW, 1.8 mg/ml) and [$^{125}$I]urokinase (0.2 μCi) in 0.1 M sodium pyrophosphate/HCl, 0.01% Tween 80, pH 8.0 buffer (0.5 ml) at 0° C. was added 2-(methoxypolyethylene (5000) glycoxymethylene)-3-methyl maleic anhydride (100 mg) maintaining the pH at 8.0 by addition of 0.1 M NaOH. After the reaction, activity in the plasminogen activation assay was found to be ca 44% of the original activity. Chromogenic substrate activity was essentially unchanged. The reaction mixture was applied to a column (5.1 ml) of Sepharose 6B CL at 4° C. and equilibrated with 0.1 M NaCl 0.05 M NaH$_2$PO$_4$/Na$_2$HPO$_4$, 0.01% Tween 80, pH 7.4. The conjugate eluted as a broad peak eluting after the column volume. Relevant fractions were pooled and the conjugate stored frozen at −40° C.

A portion of the conjugate was analysed on HPLC gel filtration. The radioactivity profile showed a broad peak eluting with an apparent molecular weight of ca. 160,000 (FIG. 2b). A portion of conjugate which had been incubated at room temperature for 3 days showed that the average molecular weight had decreased substantially to almost that of free urokinase (FIG. 2c) though clearly under these conditions 100% reversal was not obtained.

Reversal of modification was also assessed using the plasminogen activation assay. To a portion of the conjugate was added glycerol to 20% and the solution incubated at 37° C. Aliquots were assayed at intervals. Recovery of activity followed approximately first order kinetics with a pseudo first order rate constant of $3 \times 10^{-5}$ sec$^{-1}$.

(ii) A second preparation was made as follows:

Urokinase (Serono, 5 mg) was dissolved in the pyrophosphate buffer (1.2 ml) at room temperature and the reagent added in 3×250 mg portions over ca. 2 minutes with stirring. The pH was maintained at 8.0 by addition of 0.5 M NaOH from a pH stat. After base uptake had ceased the solution was applied to a column of benzamidine Sepharose (9.5 mm×11 cm bed weight) equilibrated with 0.05 M NaH$_2$PO$_4$/Na$_2$HPO$_4$, 0.1 M NaCl, 0.01% Tween 80 pH 7.4. After excess (hydrolysed) reagent had eluted, the buffer was changed to 0.5 M arginine, 0.5 M NaCl, 20 mM trishydroxymethylaminomethane, pH 7.4 whereupon the modified urokinase eluted as a single peak.

Analytical HPLC showed a broad conjugate peak (by chromogenic substrate assay of fractions), with an apparent average molecular weight of 140,000.

EXAMPLE 4

Preparation of 2-[ω-methoxypolyethyleneglycoxymethylene], 3-methylmaleyl-tissue plasminogen activator A solution of tissue plasminogen activator (t-PA) in 0.02 M NaH$_2$PO$_4$/Na$_2$HPO$_4$, 0.3 M NaCl, 0.1 M 4-guanidinobutyric acid, 0.01% Tween 80, pH 7.4 was obtained from cultured human melanoma cell supernatant by zinc chelate chromatography, affinity chromatography on lysine-Sepharose, gel filtration on Sephadex G25, repeat lysine-Sepharose chromatography, PEG dialysis, gel filtration on Sephadex G25 and repeat PEG dialysis to a concentration of 120,000 SU/ml (ca 1mg/ml). This solution (1 ml) was then gel-filtered on Sephadex G25M (PD-10, Pharmacia) into 0.1 M sodium pyrophosphate buffer pH 8.0 containing 0.1 M 4-guanidinobutyric acid and 0.01% Tween 80 (1.5 ml). The solution was stirred well at room temperature and three 250 mg portions of 2-(methoxypolyethylene(5000)glycoxymethylene)-3-methylmaleic anhydride were added at ca. 2 minute intervals, maintaining the pH at 8.0 by addition of 0.2 M NaOH from an autoburette (Radiometer). After base uptake had ceased, the solution was gel filtered at 4° C. into 0.05 M NaH$_2$PO$_4$/ Na$_2$HPO$_4$, 0.1M NaCl, 0.01% Tween 80, pH 7.4 using Sephadex G25M (2 PD-10 columns) and then applied to a column (9.5 mm×11 cm bed) of benzamidine Sepharose equilibrated with the same buffer.

After excess (hydrolysed) reagent had eluted, the buffer was changed to 0.5 M arginine, 0.5 M NaCl, 20 mM trishydroxymethylaminomethane pH 7.4 whereupon the modified protein eluted as a single peak. Relevant fractions were pooled and desalted into 100 mM NH$_4$HCO$_3$, 0.2% D mannitol using PD-10 columns. This solution was then lyophilised.

The extent and reversibility of the modification was assessed by hplc (FIG. 3). The PEG-t-PA conjugate eluted as a broad peak with an apparent molecular weight of 130,000. After 21 hours at 37° C. in 0.1 M trishydroxymethylaminomethane, 0.9% NaCl, pH 7.4 (9,900 SU/ml), the conjugate had deacylated to a large degree to an apparent molecular weight of 75,000. After 44 hours, deacylation was complete.

Methods (a) Chromogenic substrate assay

Urokinase was assayed against the chromogenic substrate S-2444 (KabiVitrum, Sweden) at a concentration of 1 mM in 0.1 M triethanolamine.HCl pH 8.0 at 25° C. An SU is defined as the amount of activity that gives an OD increase at 405 nm of 0.001/min in 1 ml of substrate in a 1 cm pathlength cell.

(b) Plasminogen activation assay

Into a cuvette was placed 10 mM S-2251 (KabiVitrum, Sweden) in 0.1 M triethanolamine buffer pH 7.0 (25 μl), 10 mg/ml lys-plasminogen (KabiVitrum, Sweden and treated with aprotinin-agarose) and the test activator at an appropriate concentration (5 μl). These were added to the cuvette without allowing the solutions to mix. To a blank cuvette was added the above solutions with the exception of the activator. The assay was initiated by addition of 0.1 M triethanolamine buffer pH 8.0 (1 ml) to both cuvettes and the OD$_{405}$ (test v. blank) monitored. The initial slope of a plot of OD against time$^2$ was taken as an arbitrary measure of the rate of plasminogen activation.

(c) γ-counting

This was performed using a Packard auto-gamma scintillation spectrometer.

(d) HPLC

Analytical gel filtration HPLC was performed on a column (SW 60 CM) of TSK G3000 SW equilibrated with 0.08 M Na$_2$HPO$_4$/NaH$_2$PO$_4$0.32 M NaCl buffer pH 7.0 containing 20% ethanol using a flow rate of 0.75 ml/min. Molecular weight calibration was achieved with standard proteins from Biorad.

(e) Assay of human plasma clot lysis

Blood (40 ml) was taken from human volunteers and mixed with 0.1 volumes 129 mM trisodium citrate. Plasma was prepared by centrifugation at 1700 g for 15 min at 4° and the plasma from 4-6 volunteers was pooled.

An aliquot (0.5 ml) of plasma was recalcified to a final concentration of 25 mM using CaCl$_2$ was supplemented with approx. 0.1 μCi [$^{125}$I]-fibrinogen (repurified by ammonium sulphate precipitation from material supplied by the Radiochemical Centre, Amersham; specific radioactivity 100 μCi/mg). The supplemented plasma was clotted onto a Nickel-chrome wire coil using 50 μl bovine thrombin (50 NIH units/ml in 0.9% NaCl). Clots were matured at 25° for 30 minutes and then washed in 6 volumes of 0.1 M phosphate buffer, pH 7.6, at 4° for 1 hour.

The clots were counted for $^{125}$I and then incubated in 3-5 ml homologous plasma, with addition of plasminogen activator, where appropriate, at 37° for up to 5 hours. Lysis was monitored by counting $^{125}$I released as fibrin degradation products. Results are expressed as the percentage release of radiolabel, allowing for the effect of taking sequential aliquots (50 μl) from the incubation volume.

(f) Assay of fibrinolytic activity in the bloodstream of guinea pigs

Male Dunkin Hartley guinea pigs (350-450 g) were anaesthetized with urethane (25% w/v solution; 6 ml/kg i.p.). One carotid artery was cannulated for collection of blood samples. One femoral vein was cannulated for injection of heparin (50 U/kg i.v.) and compound under test. Approximately 5 min after heparinization, a pre-dose blood sample (2 ml) was taken and mixed with 0.1 volumes 129 mM trisodium citrate. The compound under test was then injected (1 ml/kg) over 10s. Further blood samples were taken exactly 2, 4, 8, 16, 30, 60 and 90 min later. Heparin treatment (50 U/kg i.v.) was repeated after the 30 min sample to maintain cannula patency. All citrated blood samples were kept on ice until the end of each experiment, then centrifuged at 1700 g for 15 min at 4° to obtain plasma. Each plasma sample was diluted 200-fold in phosphate buffered saline, pH 7.4, containing 0.01% (v/v) Tween 80. Aliquots (30 μl) were then applied to fibrin plates in quadruplicate. Fibrin plates were prepared from 0.4% (w/v) human fibrinogen (Kabi, Grade L, Flow Laboratories, Scotland) dissolved in 0.029 M barbitone in 125 mM NaCl, pH 7.4, pipetted (10 ml) into 10 x 10 cm square plastic dishes (Sterilin) and clotted by rapid mixing with 0.3 ml bovine thrombin (50 NIH units/ml, Parke-Davis, U.K.). Plates were incubated at 37° for 18-24h usually, but longer if required, and stained with aqueous bromophenol blue. For each lysis zone, two diameters perpendicular to each other were measured using Vernier calipers. All diameters for each sample were averaged, and this mean converted to fibrinolytic activity by reference to a calibration curve. The latter was obtained by adding known amounts of the compound under test to the pre-dose plasma of each animal. These standards were processed using the same methods and at the same time as the experimental samples. To construct the calibration curve, diameters (mm) were plotted against $\log_{10}$ concentration of compound. The plasma concentration of compound in each experimental sample was expressed as a percentage of that expected on the basis of the dose given and the assumption of 50 ml plasma/kg body weight for each guinea pig.

RESULTS (a) Fibrinolytic activity in vitro

A urokinase conjugate prepared as described in Example 3 (ii) was compared with urokinase in the in vitro clot lysis system described above. FIG. 4 shows that at each of the concentrations tested the conjugate was initially less active (about 2-fold) than native urokinase, but that during the course of the experiment its activity increased, presumably due to release of the polymer chains. After 5 hours the extent of lysis was essentially the same for modified and unmodified urokinase.

(b) Clearance of the urokinase-PEG conjugal in guinea pigs

FIG. 5 shows the clearance of urokinase and the conjugate described in Example 3 (ii) from the bloodstream of guinea pigs. Clearly, addition of polyethylene glycol to the urokinase has caused markedly prolonged clearance.

I claim:

1. A conjugate of formula (II):

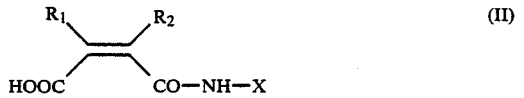

where X is a pharmaceutically useful protein and the NH moiety is derived from a protein amino group in X; and either:

(i) $R_1$ and $R_2$ are each a non-polymeric organic group or a group of formula $-R_3-P$ wherein P is a water-soluble polymer selected from the group consisting of polyethylene glycol, polypropylene glycol and methoxy polyethylene glycol and $R_3$ is a bridging group selected from the group consisting of straight or branched $C_{1-10}$ aliphatic hydrocarbon chains and straight or branched $C_{1-10}$ aliphatic hydrocarbon chains interrupted or terminated by an amide moiety, an ester moiety or at least one hetero atom selected from oxygen, sulphur or nitrogen, said moiety being unsubstituted or substituted by $C_{1-16}$ alkyl; or (ii) $R_1$ and $R_2$ together are $C_{3-5}$ polymethylene to complete a 5- to 7-membered alicyclic ring or together complete an aromatic ring, wherein the alicyclic or aromatic ring is substituted by groups $R_4$ and $R_5$ which are each of non-polymeric organic group or a group of formula $-R_3-P$; provided that at lease one of RI and $R_2$ or of $R_4$ and $R_5$ is a group $-R_3-P$.

2. A conjugate according to claim 1 in which the pharmaceutically useful protein is a fibrinolytic enzyme or pro-enzyme thereof.

3. A conjugate according to claim 1, wherein one of $R_1$ and $R_2$ is a group $P-CH_2-$ and the other is methyl.

4. A conjugate according to claim 1, wherein the water soluble polymer is methoxypolyethylene glycol.

5. A conjugate according to claim 1, wherein the pharmaceutically useful protein is tissue plasminogen activator or urokinase.

6. A process for preparing a conjugate according to claim 1 which process comprises reacting a pharmaceutically useful protein with a water-soluble polymer-containing regent comprising a group which is capable of reacting with a protein amino group or derivative thereof, to form a reversible linking group.

7. A conjugate according to claim 1, wherein $PR_3-$ is $P(CH_2)_n-$, $PO(CH_2)_nO-$, $P(CH_3)CH-$, $P(CH_3)_2C-$, $PO(CH_3)CH-$ or $PO(CH_3)_2C-$ where n is 1 to 6.

8. 2[ω-Methoxypolyethyleneglycoxymethylene]-3-methylmaleyl-human serum albumin,
2-methyl-3-[ω-methoxypolyethyleneglycoxymethylene]-maleyl-human serum albumin,
2[ω-methoxypolyethyleneglycoxymethylene]-3-methylmaleyl-urokinase,
2-methyl-3-[ω-methoxypolyethyleneglycoxymethylene]-maleyl-urokinase,
2-[ω-methoxypolyethyleneglycoxymethylene]-3-methyl-maleyl-tissue plasminogen activator or
2-methyl-3-[ω-methoxypolyethyleneglycoxymethylene]-maleyl-tissue plasminogen activator.

* * * * *

UNITED STATES PATENT AND TRADEMARK OFFICE
CERTIFICATE OF CORRECTION

PATENT NO. : 4,935,465
DATED : June 19, 1990
INVENTOR(S) : Andrew John Garman

It is certified that error appears in the above-identified patent and that said Letters Patent is hereby corrected as shown below:

Claim 1 col. 13 line 42 - "R1" should be "$R_1$"
       col. 14 line 12 - "of" should be "a"
       col. 14 line 14 - "lease" should be "least"
                and    "R1" should be "$R_1$"

Claim 7 col. 14 line 33 - "$PO(CH_2)_nO-$" should be
                        $--PO(CH_2)_n-, P(CH_2)_nO- --$ Claim 8 col. 14 line 35 - "...polyethyIene..." should be "...polyethylene..."

Signed and Sealed this

Fifth Day of January, 1993

Attest:

DOUGLAS B. COMER

Attesting Officer      Acting Commissioner of Patents and Trademarks